(12) United States Patent
Freccero et al.

(10) Patent No.: US 8,383,661 B2
(45) Date of Patent: Feb. 26, 2013

(54) 1,3 IMIDAZOLIDINE DERIVATIVES AND THEIR USE IN THE PRODUCTION OF CARBAPENEM

(75) Inventors: Mauro Freccero, Pavia (IT); Giovanni Fogliato, Barzana (IT); Antonio Manca, Milan (IT); Michele Bassanini, Casalpusterlengo (IT)

(73) Assignee: ACS DOBFAR S.p.A., Tribiano (IT)

( * ) Notice: Subject to any disclaimer, the term of this patent is extended or adjusted under 35 U.S.C. 154(b) by 290 days.

(21) Appl. No.: 12/933,756

(22) PCT Filed: Oct. 1, 2009

(86) PCT No.: PCT/EP2009/062754
§ 371 (c)(1),
(2), (4) Date: Sep. 21, 2010

(87) PCT Pub. No.: WO2010/049233
PCT Pub. Date: May 6, 2010

(65) Prior Publication Data
US 2011/0015389 A1  Jan. 20, 2011

(30) Foreign Application Priority Data

Oct. 28, 2008 (IT) .............................. MI2008A1901

(51) Int. Cl.
*A61K 31/4166* (2006.01)
*C07D 233/30* (2006.01)
(52) U.S. Cl. .................................. 514/392; 548/322.5
(58) Field of Classification Search ............... 548/322.5; 514/392
See application file for complete search history.

(56) References Cited

FOREIGN PATENT DOCUMENTS
EP    0 232 786        8/1987
EP    0232786  A1 *    8/1987

* cited by examiner

*Primary Examiner* — Kamal Saeed
*Assistant Examiner* — Janet L Coppins
(74) *Attorney, Agent, or Firm* — Oblon, Spivak, McClelland, Maier & Neustadt, L.L.P.

(57) ABSTRACT

Preparation of new heterocyclic compounds characterized by 1,3-imidazolidine structure useful for stereoselective synthesis of optically pure key intermediates in 1β-methylcarbapenem production.

18 Claims, No Drawings

1,3 IMIDAZOLIDINE DERIVATIVES AND THEIR USE IN THE PRODUCTION OF CARBAPENEM

The present invention relates to 1,3 imidazolidine intermediates useful in the stereoselective synthesis of carbapenem, in particular of 1β-methylcarbapenem.

The heterocyclic compounds of this invention are represented in formula (I),

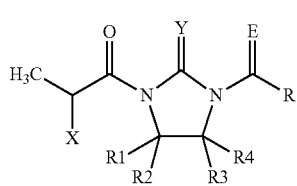

(I)

in which X is a halogen chosen from chlorine, bromine and iodine, Y is chosen from the group consisting of oxygen, sulphur and $NR_5$, where $R_5$ is $(C_1-C_9)$aliphatic, $(C_3-C_8)$alicyclic, $(C_3-C_9)$heterocyclic, phenyl, aryl or heteroaryl carrying up to three substituents chosen from halogen, nitro group, $(C_1-C_3)$alkoxy, E is chosen from the group consisting of oxygen and sulphur, R is is chosen from the group consisting of hydrogen, methyl, ethyl, propyl, isopropyl, $(C_4-C_9)$aliphatic alkyl, $(C_3-C_9)$alicyclic alkyl, 1-haloethyl(—CHX—$CH_3$) only when E is oxygen, aryl, heteroaryl, aryl$(C_1-C_3)$alkyl, heteroaryl$(C_1-C_3)$alkyl, $(C_1-C_9)$aliphatic alkyloxy, $(C_3-C_9)$alicyclic alkyloxy, aryloxy, heteroaryloxy, aryl$(C_1-C_3)$alkyloxy, heteroaryloxy, heteroaryl$(C_1-C_3)$alkyloxy, $(C_1-C_9)$aliphatic alkylthio, $(C_3-C_9)$alicyclic alkylthio, arylthio, heteroarylthio, aryl$(C_1-C_3)$alkylthio, heteroarylthio, heteroaryl$(C_1-C_3)$alkylthio, while $R_1$, $R_2$, $R_3$ and $R_4$ are independently chosen from the group consisting of hydrogen, methyl, ethyl, $(C_3-C_9)$aliphatic alkyl, $(C_3-C_9)$alicyclic alkyl, heteroaryl, heteroaryl$(C_1-C_3)$alkyl, aryl, aryl$(C_1-C_3)$alkyl, possibly mutually combined to form an o-phenylene structure with the 1,3 imidazolidine ring, such as a benzo[d]-2,3-dihydro-1H-imidazole structure, and, when $R_1$ is coupled to $R_2$ and $R_3$ is coupled to $R_4$, they mutually combine to form an alkylene group or a cyclic spiro structure, such as ligands of heterocyclo 1,3-imidazolidine.

As they are derived from a 2-halopropionic acid ($CH_3$—CHX—COOH in which X has the aforedefined meaning), the compounds of formula (I) are used for the stereoselective synthesis of the advanced intermediate of formula (II),

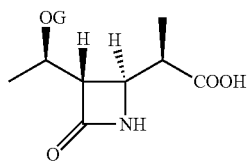

(II)

a key chiral intermediate for the synthesis of various 1β-methylcarbapenems, where G is chosen from the group consisting of hydrogen and hydroxyl protective groups [from those described in various texts, such as "Protective Groups in Organic Synthesis" (1981) (published by John Wiley & Sons, New York, U.S.A.), "New Experimental Chemistry" (Shin-Jikken Kagaku Koza" in Japanese) Vol. 14 (1978) (published by Maruzen, Tokyo, Japan), "Chimica Organica Applicata" (author Umberto Valcavi), published by CLUED, Milan, Italy, ISBN 88-7059-041-0) and in the references mentioned in these three texts], i.e. $(C_1-C_4)$alkyl, methoxymethyl, methylthiomethyl, allyl, propargyl, methoxyethoxymethyl, $(C_1-C_9)$dialkylboryl, 9-borabicyclonon-9-yl, 2,2,2-trichloroethoxymethyl, tetrahydropyranyl, substituted ethyls chosen from 1-ethoxyethyl, 1-methyl-1-methoxyethyl, trichloroethyl, hence methyls substituted with aryls chosen from phenylmethyl, diphenylmethyl, triphenylmethyl, p-methoxyphenylmethyl, o-nitrophenylmethyl, p-nitrophenylmethyl, p-chlorophenylmethyl, diphenylmethyl, triphenylmethyl, and in addition substituted silyls chosen from the trimethylsilyl, triethylsilyl, t-butyldimethylsilyl, or t-butyldiphenylsilyl group, and moreover formyloyl, $(C_1-C_5)$alkanoyl, halogenated $(C_1-C_3)$alkanoyl, aryloyl chosen from benzoyl, p-methylbenzoyl, naphthoyl, and in addition $(C_1-C_4)$alkoxycarbonyl [preferably chosen from methoxycarbonyl, ethoxycarbonyl, isobutoxycarbonyl], halogenated ethoxycarbonyl [preferably chosen from 2-iodo-ethoxycarbonyl and 2,2,2-trichloroethoxycarbonyl], $(C_3-C_5)$alkenylcarbonyl [preferably chosen from allyloxycarbonyl, 3-methylallyloxycarbonyl], and arylmethoxycarbonyl [preferably chosen from phenyl methoxycarbonyl, p-methoxyphenylmethoxycarbonyl, 2,4-dimethoxyphenyl methoxycarbonyl, o-nitrophenylmethoxycarbonyl, p-nitrophenylmethoxycarbonyl].

The compounds of formula (II) are known key chiral intermediates in the synthesis of 1β-methylcarbapenem with antimicrobic activity.

The compounds of formula (II) are known to have been synthesized by various strategies, in particular as described and claimed in EP232786B1, by derivatives of a 2-halopropionic acid binding heterocycles different from those described in the present invention.

Likewise to that described in EP232786B1, the compounds of formula (I) also react as enolates of a 2-halopropionic acid derivative with azetidinone intermediates of formula (III),

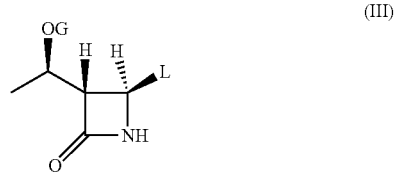

(III)

where G has the meaning described for the compounds of formula (II) while L is a nucleofugal ligand chosen from the group consisting of halogen, formyloyloxy, acetoxy, $(C_2-C_5)$alkylcarbonyloxy, $(C_3-C_9)$cycloalkylcarbonyloxy, $(C_1-C_5)$acyloxy chosen from unsaturateds and halogenates in a position vicinal to the carbonyl, arylcarbonyloxy [preferably chosen from benzoyloxy, p-methylbenzoyloxy, p-methoxybenzoyloxy, p-chlorobenzoyloxy, p-nitrobenzoyloxy], $(C_1-C_7)$alkylsulphonyloxy, arylsulphonyloxy [preferably chosen from phenylsulphonyloxy, p-chlorophenylsulphonyloxy, p-methylphenylsulphonyloxy], $(C_1-C_7)$alkylsulphonyl, arylsulphonyl [preferably chosen from phenylsulphonyl, p-chlorophenylsulphonyl, p-methylsulphonyl], $(C_1-C_7)$alkylsulphinyl, arylsulphinyl [preferably chosen from phenylsulphinyl, p-chlorophenylsulphinyl, p-methylphenylsulphinyl], and finally $(C_1-C_7)$alkylsulphenyl and arylsulphenyl [preferably chosen from phenylsulphenyl and p-chlorophenylsulphenyl]: the nature of the nucleofuge L is functional on the condensation between the species (I), activated as enolate, and the species (III), to obtain the new intermediate species (IIIb),

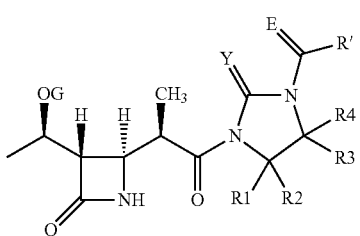

(IIIb)

where G, Y, E, $R_1$, $R_2$, $R_3$ and $R_4$ have the meanings described for the compounds (I) and (II), while R' is chosen from the group consisting of hydrogen, methyl, ethyl, propyl, isopropyl, $(C_4-C_9)$aliphatic alkyl, $(C_3-C_9)$alicyclic alkyl, heteroaryl, aryl$(C_1-C_3)$alkyl, heteroaryl$(C_1-C_3)$alkyl, $(C_1-C_9)$ aliphatic alkyloxy, $(C_3-C_9)$alicyclic alkyloxy, aryloxy, heteroaryloxy, aryl$(C_1-C_3)$alkyloxy, heteroaryloxy, heteroaryl$(C_1-C_3)$alkyloxy, $(C_1-C_9)$aliphatic alkylthio, $(C_3-C_9)$ alicyclic alkylthio, arylthio, heteroarylthio, aryl$(C_1-C_3)$alkylthio, heteroarylthio, heteroaryl$(C_1-C_3)$alkylthio.

The present inventors have surprisingly verified that the intermediate species (IIIb) is isolated stereoisomerically pure, i.e. the formal addition of the species (I)-derived enolate to the species (III) has produced the species (IIIb) by stereospecific and stereoselective reactivity.

The species (IIIb) presents four contiguous stereocentres identifiable by the common graphic ligand describers used in the relative structural formulas, each characterized by a graphically explicit unequivocal absolute configuration. The formal stereospecific addition comprises the initial elimination of the nucleofugal species L, as HL, from the azetidinone species (III), by the formation of the corresponding transient azetinone intermediate (IIIc),

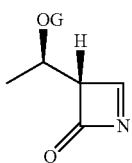

(IIIc)

on which the enolate deriving from the species (I) is stereospecifically added by the mechanism described in the review of Andrew H. Berks "Preparation of Two Pivotal Intermediates for the Synthesis of 1β-Methyl Carbapenem Antibiotics", Tetrahedron, (1996) 52(2) pages 331-375: hence from that stated, the formation of the species (IIIb) resulting from the addition of the species (I)-derived enolate to the species (III), with elimination of the species HL, takes place by an elimination-addition mechanism.

The present inventors have also surprisingly verified that the compounds (Ib), included in the compounds of formula (I),

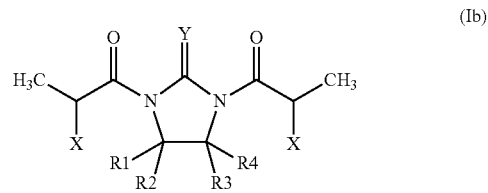

(Ib)

where E is equal to oxygen and R is equal to 1-haloethyl, have the peculiar structural characteristic of comprising two equal ligands, each of which is able to locate a carbanion of enolate type on the carbon vicinal to the carbonyl.

The species (Ib) is therefore a heterocyclic structure able to generate two carbanions, hence behaving as a bidentate reagent; in particular, this is characteristic has proved surprisingly advantageous when it has been found that the first carbanion formed on one of the ligands operates as base on the species (III) to form the reactive intermediate (IIIc), then subsequently the second carbanion formed on the other ligand is able to add as nucleophile to the just formed species (IIIc), to obtain the species (IIId),

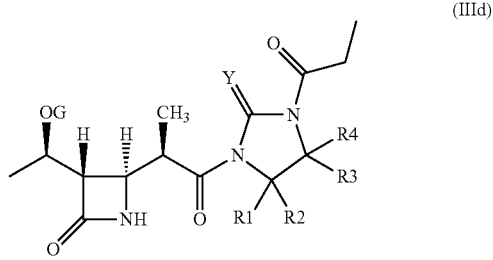

(IIId)

included in the products of formula (IIIb).

Consequently, to obtain the stereoisomerically pure species (IIId), the compounds (Ib) are advantageously usable in molar quantities less even than 50% compared with other heterocyclic derivatives of a 2-halopropionic acid known up to the present time in the state of the art, precisely because they display double enolate characteristics, i.e. bifunctional or "bidentate", as schematized below,

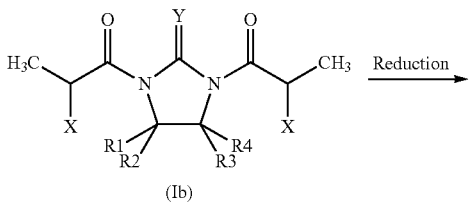

(Ib)

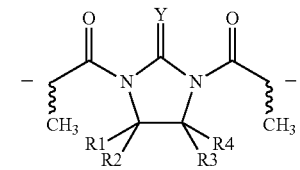

Double or "bidentate" enolate able to act both as a base on the amide nitrogen of the species (III) and as a nucleophile on the transient reactive intermediate (IIIc) thus formed, in accordance with the following scheme.

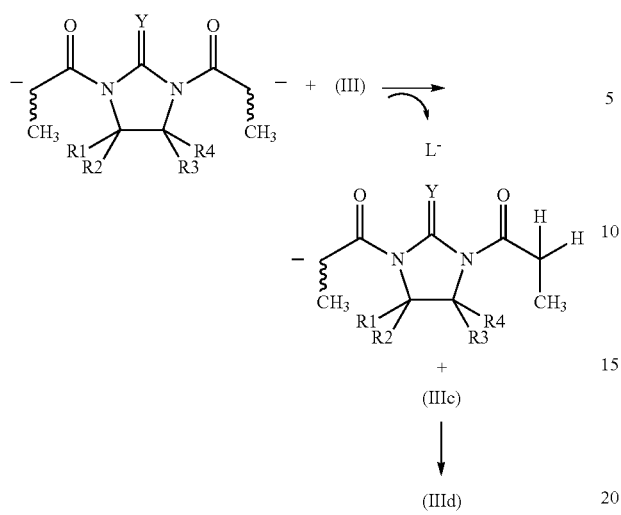

(IIIc)

↓

(IIId)

is Any other monofunctional enolate ("monodentate"), such as all those known up to the present time in the state of the art, is used in large excess because it has initially to act as a base to obtain the species (IIIc), then as a nucleophile to obtain the addition product; in this respect, as is apparent from the experimental examples of EP232786B1, the highest yields are achieved using at least two molar equivalents of the chosen heterocyclic derivative of 2-halopropionic acid with respect to the reacting species (III).

The species (IIIb) is then transformed directly into the species (II) by treatment with hydrogen peroxide in the presence of an alkali metal hydroxide and with the final addition of a reducing species, preferably sodium sulphite.

As an alternative to the above direct transformation, the species (IIIb) can be transformed into the species (IIIe),

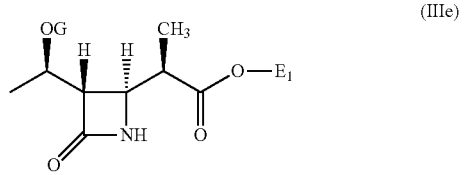

(IIIe)

where G has the meaning defined for the compounds of formula (IIIb), while $E_1$ is chosen from the group consisting of $(C_1-C_4)$alkyl, allyl, arylmethyl, diarylmethyl, triarylmethyl, in which each aryl substituent can optionally present, as aromatic ring ligands, up to three substituents independently chosen from the group consisting of nitro, $(C_1-C_4)$alkyl, $(C_1-C_4)$alkoxy, fluorine, chlorine, bromine and iodine.

Hence, the compounds of formula (II) are obtained from the species (IIIe) by the procedure described in EP232786B1, or by other known methods for deprotecting esters, by means for example of the use of palladium complexes in the case in which $E_1$ is an allyl group.

The species (II) is obtained stereoisomerically pure both from compounds of formula (IIIb) and from derivatives of formula (IIIe).

The compounds of formula (I) are synthesized starting from the compounds (IV),

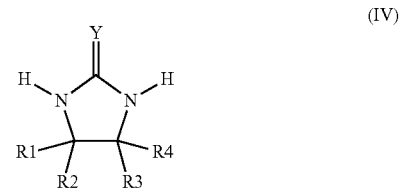

(IV)

where Y, $R_1$, $R_2$, $R_3$ and $R_4$ have the meaning described for the compounds of formula (I), prepared as described in U.S. Pat. No. 4,681,948, EP232786B1 and EP573667B1 and, for a general approach to the synthesis of 2-imino-1,3-imidazolidine heterocycles, in "Best Practice & Research Clinical Anaesthesiology", 14(2), 237-246 (2000), also considering the references mentioned in said four documents.

Firstly, a compound included in those described in formula (IV) is reacted in the presence of a base chosen from alkali metal hydrides, $(C_1-C_4)$alkyllithium derivatives, aryllithium derivatives, heteroaryllithium derivatives and alkali metals with up to one or less than one molar equivalent of an activated derivative of formula (V),

(V)

where E and R have the meaning described for the compounds of formula (I), while $Y_1$ is a nucleofugal group typical of acylation reactions [preferably chosen from the group consisting of chlorine, bromine and iodine, independently of X], in at least one aprotic inert solvent, preferably chosen from tetrahydrofuran, dioxane, 1,2-dimethoxyethane, $C_6$ alicyclic hydrocarbons, $(C_6-C_{10})$aliphatic hydrocarbons, benzene, $(C_1-C_3)$alkylsubstituted benzene, $(C_1-C_3)$dialkylsubstituted benzene, $(C_1-C_3)$ trialkylsubstituted benzene, halogenated $(C_1-C_3)$aliphatic hydrocarbons, glyme, diglyme, di$(C_1-C_4)$ alkylethers, N,N-dimethylacetamide, N,N-dimethylformamide, N-methylpyrrolidone and hexamethylphosphoramide, at temperatures between −80° C. and +50° C., to obtain the intermediate (IVbis)

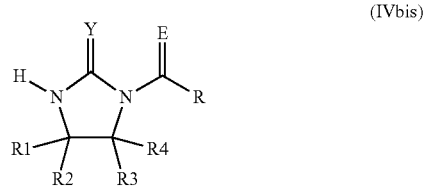

(IVbis)

which, even non-isolated, is made to react with a further equivalent of a base chosen from those mentioned in at least one aprotic inert solvent, possibly in mixture with other solvents of the same type, then adding at least one molar equivalent of 2-halopropionyl derivative (VI)

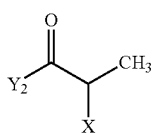

(VI)

where X has the same meaning as for the compounds of formula (I) and $Y_2$ is a nucleofugal group typical of acylation reactions [preferably chosen from the group consisting of chlorine, bromine and iodine, independently of X], at temperatures between $-80°$ C. and $+50°$ C., to isolate the compound (I).

If the compound (Ib) is synthesized, i.e. when the reagent (V) coincides with the reagent (VI), the corresponding diastereoisomers (Ic), (Id), (Ie) and (If)

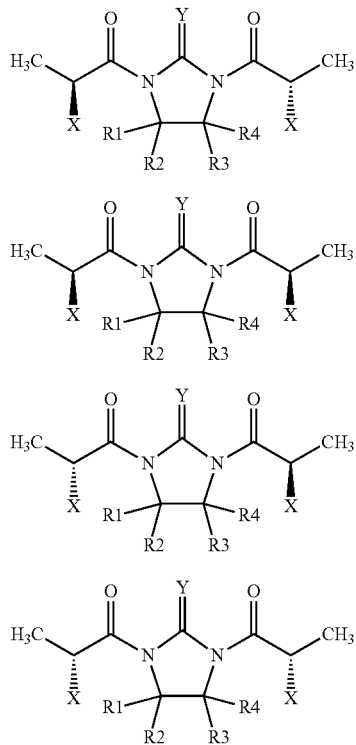

can be obtained.

If $R_1$, $R_2$, $R_3$ and $R_4$ are in the form of identical pairs, with $R_2$ equal to $R_3$ and $R_1$ equal to $R_4$, and the equal substituents of said pairs are mutually correlatable by trans stereochemistry, (Ic) and (Ie) are diastereoisomers while (Id) and (If) coincide, whereas when the equal substituents of said pairs are mutually correlatable by cis stereochemistry, (Ic) and (Ie) are enantiomers, hence isolated together as racemate, while (Id) and (If) are diastereoisomers, whereas in contrast, if $R_1$, $R_2$, $R_3$ and $R_4$ are identical, (Ic) and (Ie) are enantiomers and are isolated together as racemate, while (Id) and (If) coincide in a single mesoform.

Subsequently, the compounds of formula (I) react with the compounds (III) to obtain the intermediates (IIIb) as pure stereoisomer, in accordance with Reformatsky-type reactivity, in the presence of powdered zinc or other reducers described in the report Tetrahedron 60 (2004), 9325-9374 (report 692).

It has also been verified that the reaction of adding the appropriate species (Ib) to the species (IIIc) deriving from the species (III) enables the intermediate species (IIId) to be obtained, with G equal to t-butyldimethylsilyl, Y equal to oxygen, $R_1=R_2=R_3=R_4$=methyl, as pure diastereoisomer with reproducible higher yields when, of the possible choices for the species (Ib), the racemate (Ic)+(Ie) is preferred to the mesoform (Id); in addition the mesoform (Id) can itself be advantageously transformed into the more efficient racemate (Ic)+(Ie) by catalyzed acid rebalancing in solution in which the $sp^3$ carbon atoms are inverted as stereocentres binding the group X so that the racemate/mesoform diastereoisomeric ratio, from the equilibrium viewpoint, is about 65/35, to hence display an overall enrichment in the sought racemate of the resultant solution which is then isolated in solid form by known chromatographic methods.

The compound (I) and the powdered zinc can be used in molar excess to increase the condensation yield to obtain the intermediate (IIIb): the zinc is used in a quantity from 1 to 5 molar equivalents, preferably from 2 to 5 molar equivalents, with respect to the substrate (III), while the compound (I) is used from 0.5 to 3 molar equivalents, preferably from 1 to 3 molar equivalents, with respect to the substrate (III). If the compound (I) used is the diastereoisomerically pure compound (Id), the reaction displays high yields of the stereoisomerically pure intermediate (IIId) even with 1 molar equivalent of zinc and 0.5 molar equivalents, with respect to the substrate (III), of (Id) which, in this case, is the limiting agent of the reaction. The condensation reaction between the compounds of formula (I) and (III), for formation of the intermediate (IIIb), is conducted at temperatures between $-50°$ C. and $+150°$ C., preferably between $0°$ C. and $100°$ C.

The species (IIIb) is then directly transformed into the species (II) by treatment with hydrogen peroxide, used from 1 to 20 molar equivalents with respect to the substrate (IIIb), in the presence of an alkali metal hydroxide (preferably lithium hydroxide) used from 1 to 10 molar equivalents with respect to the substrate (IIIb), in aqueous organic solvents chosen from dioxane, tetrahydrofuran, N,N-dimethylformamide, $(C_1-C_4)$aliphatic alcohols, N,N-dimethylacetamide and N-methylpyrrolidone at a reaction temperature between $-10°$ C. and $+30°$ C., and adding a reducing species, preferably sodium sulphite, on reaction termination.

Alternatively, the intermediate (IIIb) is added in a $(C_1-C_4)$ aliphatic alcohol in the presence of an alkali metal carbonate or alcoholate of the $(C_1-C_4)$aliphatic alcohol chosen as solvent, or adding the species (IIIb) in an aprotic inert solvent chosen from $(C_1-C_4)$alkylethers, tetrahydrofuran, dioxane, 1,2-dimethoxyethane, glyme, diglyme, $(C_6-C_{10})$aliphatic hydrocarbons, $(C_7-C_9)$alicyclic hydrocarbons, cyclohexane, cyclohexene, benzene, toluene, and other aromatic hydrocarbons, polar aprotic solvents chosen from N,N-dimethylformamide, N,N-dimethylacetamide, N-methylpyrrolidone, hexamethylphosphoramide, in the presence of a $(C_1-C_4)$aliphatic alcoholate or an arylmethoxylate or a diarylmethoxylate or a triarylmethoxylate of an alkali metal, in which each aryl substituent can optionally present, as aromatic ligands, up to three substituents independently chosen from the group consisting of nitro, $(C_1-C_4)$alkyl, $(C_1-C_4)$alkoxy, leaving the mixture to react for about 1 hour at a temperature between $-20°$ C. and $+50°$ C. to obtain the species (IIIe), which is then transformed into the optically pure key intermediate (II), as illustrated in EP232786B1.

Proposed non-limiting experimental examples of the invention are described below.

EXAMPLES 1-a AND 1-b

Preparation and Isolation of the Diastereoisomers (Ic) and (Id), with X=Bromine, Y=Oxygen, $R_1=R_2=R_3=R_4$=Methyl

Example 1-a 200 mg of the compound (IV), with $R_1=R_2=R_3=R_4$=methyl and Y=oxygen are suspended in 10 ml of anhydrous tetrahydrofuran in a 50 ml 4-neck flask under an inert argon atmosphere. The suspension is cooled for 5 minutes to 0° C. in an ice bath. 1.8 ml of 1.6M n-butyllithium in hexane are added in two portions under strong agitation, the solution becoming clear after a few minutes. It is agitated for 10 minutes at 0° C. It is then poured (under an inert argon atmosphere) through a narrow tube dropwise into a solution of 2-bromopropionyl bromide (317 µl; 3.0 mmoles) in 5 ml of tetrahydrofuran under energetic agitation, maintained at 0° C. in an ice bath. The addition lasts about 20 minutes. It is left under agitation at 0° C. for 10 minutes, and then at ambient temperature for 30 min.

The reaction is then quenched by adding 20 ml of phosphate buffer at pH 6.5. The tetrahydrofuran is evaporated in a rotavapor. The aqueous solution containing white crystals in suspension is extracted 3 times with ethyl acetate, and dried over sodium sulphate for 30 min at 0° C. It is filtered and evaporated to obtain 560 mg of crude residue consisting of the diastereoisomers (Ic) and (Id).

The diastereoisomers obtained are separated by chromatography on a silica gel column, eluting with a 9/1 v/v cyclohexane/ethyl acetate solution, to obtain 302 mg of compound (Ic) as racemate (Ic)+(Ie), and 255 mg of compound (Id) as single mesoform.

$^1$HNMR-CDCl$_3$—300 MHz: (Ic)+(Ie) (racemate) 1.45 ppm (singlet, 12H), 1.85 ppm (doublet, J=6.6 Hz, 6H), 5.84 ppm (quartet, 4H), (Id) 1.44 ppm (singlet, 6H), 1.46 ppm (singlet 6H), 1.84 ppm (doublet, J=6.6 Hz, 6H), 5.75 ppm (quartet, 4H). The structure and the absolute configuration of the obtained compounds were defined by analyzing the values of the chemical shifts of the two products and by PM3 computational analysis.

Example 1-b

The reaction of example 1-a was repeated starting from 1.0 g of compound (IV), to obtain 2.8 mg of crude residue consisting of the diastereoisomers (Ic) and (Id). The diastereoisomers obtained are separated by chromatography on an MPLC column, eluting with a 95/5 v/v cyclohexane/ethyl acetate solution, by means of a Biotage 50 g KP-SIL Snap Flash cartridge column, flow 30 ml/min, to obtain 1.5 g of compound (Ic) as racemate (Ic)+(Ie) (product least retained in the column with Rf=0.71), and 1.2 g of compound (Id) (product most retained in the column with Rf=0.40), as single mesoform.

$^1$HNMR-CDCl$_3$—300 MHz: the $^1$HNMR characterizations for compound (Ic)+(Ie) (racemate) and compound (Id) (mesoform) are superimposable on those described in example 1-a. The structure and the absolute configuration of the obtained compounds were confirmed by analyzing the values of the chemical shifts of the two products and by PM3 computational analysis.

EXAMPLE 2

Conversion of the Mesoform (Id) into the Corresponding Racemate (Ic)+(Ie), with $R_1=R_2=R_3=R_4$=Methyl, Y=Oxygen and X=Bromine 200 mg of the product (Id) are fed into 50 ml of acetonitrile to which 0.5 ml of 65% w/w aqueous hydrobromic acid are added and the mixture agitated for about 4 hours until equilibrium is reached in which the racemate/mesoform ratio is about 65/35. The solution is evaporated in a rotavapor to obtain 200 mg of a crude product consisting of 32.5% (Ic), 32.5% (Ie) and 35% (Id), hence purifiable by chromatography, on the basis of that indicated above for example 1-a and example 1-b, to isolate the raceme product (Ic)+(Ie) in pure form.

EXAMPLES 3-a, 3-b AND 3-c

Preparation of the Intermediate (IIId), with Y=Oxygen, G=T-Butyldimethylsilyl, $R_1=R_2=R_3=R_4$=Methyl

Example 3-a 431 mg of compound (III), with G=t-butyldimethylsilyl and L=acetoxy, are dissolved into 3 ml anhydrous tetrahydrofuran in the presence of 121.4 mg of activated powdered zinc under an inert argon atmosphere. 6 ml of a solution in anhydrous tetrahydrofuran of 306 mg of compound (Ic) (as racemate) are added dropwise over a time of 50 minutes to the suspension, agitated magnetically and heated under reflux by a bath at +90° C. The mixture is then heated under reflux for a further 30 minutes. It is allowed to cool to ambient temperature under agitation for 15 minutes. The mixture is then cooled to 0° C., then adding 20 ml of a phosphate buffer at pH 6.5, to precipitate a crystalline white solid. The tetrahydrofuran is removed from the mixture by evaporation under reduced pressure. The aqueous solution obtained is extracted three times with ethyl acetate. The organic phase is washed once with water and dried with sodium sulphate for 12 hours at −10° C. The crude reaction product is purified by chromatography on a silica gel column, eluting with a cyclohexane/ethyl acetate solution at a gradient starting from 9/1 v/v cyclohexane/ethyl acetate, until the cyclohexane/ethyl acetate ratio=7/3 v/v.: 13 mg of product (IIId) are obtained.

$^1$HNMR-CDCl$_3$—300 MHz: (IIId) 0.09 ppm (singlet, 6H), 0.89 ppm (singlet, 9H), 1.13-1.24 ppm (9H), 1.39-1.44 ppm (12H), 2.87 ppm (multiplet, 1H), 2.94 ppm (multiplet, 1H), 3.06 (multiplet, 1H), 3.96 ppm (multiplet, 1H), 4.12 ppm (multiplet, 1H), 4.22 ppm (multiplet, 1H), 5.91 (singlet, 1H).

Example 3-b 582 mg of compound (III), with G=t-butyldimethylsilyl and L=acetoxy, are dissolved in 3 ml anhydrous tetrahydrofuran in the presence of 219 mg of activated powdered zinc under an inert argon atmosphere. 14 ml of a solution of 700 mg of compound (Ic) (as racemate) are added dropwise over a time of 50 minutes to the suspension, agitated magnetically and heated under reflux by a bath at +90° C. The mixture is then heated under reflux for a further 30 minutes. It is allowed to cool to ambient temperature under agitation for 15 minutes. The mixture is then cooled to 0° C., then adding 40 ml of a phosphate buffer at pH 6.5, to precipitate a crystalline white solid. The tetrahydrofuran is removed from the mixture by evaporation under reduced pressure. The aqueous solution obtained is extracted three times with ethyl acetate. The organic phase is washed once with water and dried with sodium sulphate for 12 hours at −10° C.

The dried solution is then evaporated and the crude reaction product is purified by chromatography on an MPLC column with silica gel (column: Biotage 50 g KP-SIL Snap Flash cartridge, flow 30 ml/min) eluting with an 8/2 v/v cyclohexane/ethyl acetate solution, 746 mg of product (IIId) are obtained.

$^1$HNMR-CDCl$_3$—300 MHz: the $^1$HNMR characterization for compound (IIId) is superimposable on that described in example 2-a.

Example 3-c

The procedure of example 3-a is followed but using 102 mg of compound (III), with G=t-butyldimethylsilyl and L=acetoxy, in the presence of 29 mg of activated powdered zinc and 73 mg of compound (Id) (mesoform) instead of (Ic).

After chromatographic purification as described in example 2, 70 mg of product (IIId) are obtained.

$^1$HNMR-CDCl$_3$—300 MHz: the $^1$HNMR characterization for compound (IIId) is superimposable on that described in example 2-a.

EXAMPLE 4

Preparation of the Compound of Formula (II), with G=T-Butyldimethylsilyl 355 mg of 37% hydrogen peroxide (3.12 mmol) followed by 71 mg of lithium is hydroxide monohydrate (1.8 mmol) are added under agitation to a 0.05M solution consisting of 300 mg (0.65 mmol) of compound (111b), with G=t-butyldimethylsilyl, Y and E both equal to oxygen, R'=ethyl, $R_1=R_2=R_3=R_4$=methyl, dissolved in a solution consisting of tetrahydrofuran/water=3/1 v/v cooled to 0° C. The mixture is agitated for 1 hour at 0° C., monitoring the disappearance of the substrate (IIIb) by TLC (eluent cyclohexane/ethyl acetate=8/2 v/v). At the end of the reaction sufficient sodium sulphite is added to eliminate the peroxides, as evaluated by starch-iodine paper. The tetrahydrofuran is then evaporated in a rotavapor and the aqueous phase acidified with 10% w/w aqueous hydrochloric acid until a white precipitate appears which is extracted with three 10 ml portions of ethyl acetate. The organic solution obtained is dried over sodium sulphate and evaporated in a rotavapor to obtain 190 mg of the compound of formula (II) in solid form.

The invention claimed is:

1. A heterocyclic compound of formula (I):

(I)

wherein:

X is a halogen selected from the group consisting of chlorine, bromine and iodine;

Y is selected from the group consisting of oxygen, sulphur and NR$_5$;

R$_5$ is (C$_1$-C$_9$)aliphatic, (C$_3$-C$_9$)alicyclic, (C$_3$-C$_9$)heterocyclic, phenyl, aryl, or heteroaryl carrying up to three substituents selected from the group consisting of halogen, nitro group, and (C$_1$-C$_3$)alkoxy;

E is selected from the group consisting of oxygen and sulphur;

R is selected from the group consisting of hydrogen, methyl, ethyl, propyl, isopropyl, (C$_4$-C$_9$)aliphatic alkyl, (C$_3$-C$_9$)alicyclic alkyl, and 1-haloethyl(—CHX—CH$_3$) only when E is oxygen, aryl, heteroaryl, aryl(C$_1$-C$_3$) alkyl, heteroaryl(C$_1$-C$_3$)alkyl, (C$_1$-C$_9$)aliphatic alkyloxy, (C$_3$-C$_9$)alicyclic alkyloxy, aryloxy, heteroaryloxy, aryl(C$_1$-C$_3$)alkyloxy, heteroaryl(C$_1$-C$_3$)alkyloxy, (C$_1$-C$_9$)aliphatic alkylthio, (C$_3$-C$_9$)alicyclic alkylthio, arylthio, heteroarylthio, aryl(C$_1$-C$_3$)alkylthio, and heteroaryl(C$_1$-C$_3$)alkylthio;

R$_1$, R$_2$, R$_3$ and R$_4$ are independently selected from the group consisting of hydrogen, methyl, ethyl, (C$_3$-C$_9$) aliphatic alkyl, (C$_3$-C$_9$)alicyclic alkyl, heteroaryl, heteroaryl(C$_1$-C$_3$)alkyl, aryl, and aryl(C$_1$-C$_3$)alkyl, optionally mutually combined to form an o-phenylene structure with the 1,3 imidazolidine ring, such as a benzo [d]-2,3-dihydro-1H-imidazole structure, and, such that when R$_1$ is coupled to R$_2$ and R$_3$ is coupled to R$_4$, they mutually combine to form an alkylene group or a cyclic spiro structure, such as ligands of heterocyclo 1,3-imidazolidine.

2. The compound of claim 1, wherein Y and E are independently selected from the group consisting of oxygen and sulphur.

3. The compound of claim 1, wherein E is oxygen and R is 1-haloethyl(—CHX—CH$_3$).

4. The compound of as claimed in claim 1, wherein:

E represents oxygen; and

R is 1-haloethyl(—CHX—CH$_3$), such that the absolute configuration of each of the two stereocentres binding a substituent X is graphically schematized in the following formulas (Ic), (Id), (Ie) and (If):

(Ic)

(Id)

(Ie)

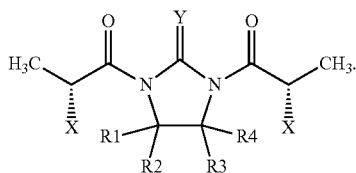

(If)

5. A heterocyclic compound of formula (IIIb):

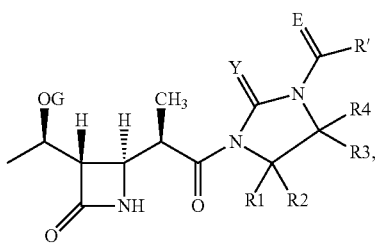

(IIIb)

wherein:

Y is selected from the group consisting of oxygen, sulphur and $NR_5$;

E is selected from the group consisting of oxygen and sulphur;

$R_1$, $R_2$, $R_3$ and $R_4$ are independently selected from the group consisting of hydrogen, methyl, ethyl, ($C_3$-$C_9$) aliphatic alkyl, ($C_3$-$C_9$)alicyclic alkyl, heteroaryl, heteroaryl($C_1$-$C_3$)alkyl, aryl, and aryl($C_1$-$C_3$)alkyl, optionally mutually combined to form an o-phenylene structure with the 1,3 imidazolidine ring, such as a benzo[d]-2,3-dihydro-1H-imidazole structure, and, such that when $R_1$ is coupled to $R_2$ and $R_3$ is coupled to $R_4$, they mutually combine to form an alkylene group or a cyclic spiro structure, such as ligands of heterocyclo 1,3-imidazolidine;

G is selected from the group consisting of hydrogen, ($C_1$-$C_4$)alkyl, methoxymethyl, methylthiomethyl, allyl, propargyl, methoxyethoxymethyl, ($C_1$-$C_9$)dialkylboryl, 9-borabicyclonon-9-yl, 2,2,2-trichloroethoxymethyl, tetrahydropyranyl, a substituted ethyl group selected from the group consisting of 1-ethoxyethyl, 1-methyl-1-methoxyethyl, and trichloroethyl, an aryl-substituted methyl group selected from the group consisting of phenylmethyl, diphenylmethyl, triphenylmethyl, p-methoxyphenylmethyl, o-nitrophenylmethyl, p-nitrophenylmethyl, and p-chlorophenylmethyl, a substituted silyl group selected from the group consisting of trimethylsilyl, triethylsilyl, t-butyldimethylsilyl, and t-butyldiphenylsilyl group, formyl, ($C_1$-$C_5$)alkanoyl, halogenated ($C_1$-$C_3$)alkanoyl, an aryloyl selected from the group consisting of benzoyl, p-methylbenzoyl, and naphthoyl, ($C_1$-$C_4$)alkoxycarbonyl, halogenated ethoxycarbonyl, ($C_3$-$C_5$)alkenylcarbonyl and arylmethoxycarbonyl; and R' is selected from the group consisting of hydrogen, methyl, ethyl, propyl, isopropyl, ($C_4$-$C_9$)aliphatic alkyl, ($C_3$-$C_9$)alicyclic alkyl, aryl, heteroaryl, aryl($C_1$-$C_3$) alkyl, heteroaryl($C_1$-$C_3$)alkyl, ($C_1$-$C_9$)aliphatic alkyloxy, ($C_3$-$C_9$)alicyclic alkyloxy, aryloxy, heteroaryloxy, aryl($C_1$-$C_3$)alkyloxy, heteroaryloxy, heteroaryl($C_1$-$C_3$) alkyloxy, ($C_1$-$C_9$)aliphatic alkylthio, ($C_3$-$C_9$)alicyclic alkylthio, arylthio, heteroarylthio, aryl($C_1$-$C_3$)alkylthio, heteroarylthio, and heteroaryl($C_1$-$C_3$)alkylthio.

6. The compound of claim 5, wherein Y and E are independently selected from the group consisting of oxygen and sulphur.

7. The compound of claim 5, wherein:

E is oxygen;

R' is ethyl; and

G is selected from the group consisting of hydrogen, trimethylsilyl, triethylsilyl, t-butyldimethylsilyl, and t-butyldiphenylsilyl.

8. The compound of claim 5, wherein:

Y and E are oxygens

R' is ethyl; and

G is hydrogen.

9. The compound of claim 5, wherein:

Y and E are oxygen;

$R_1$, $R_2$, $R_3$ and $R_4$ are methyl;

R' is ethyl; and

G is t-butyldimethylsilyl.

10. A process for preparing the compound of claim 1, the process comprising reacting a compound of formula (IV):

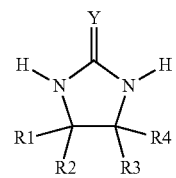

(IV)

with up to one or less than one molar equivalent of an activated derivative of formula (V):

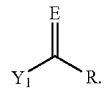

(V)

in the presence of a first base, in at least one first aprotic inert solvent, at temperatures between −80° C. and +50° C., to obtain an intermediate (IVbis):

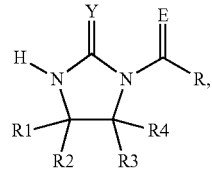

(IVbis)

and reacting the intermediate (IVbis) with a further equivalent of a second base, in a second aprotic inert solvent, then adding at least one molar equivalent of a 2-halopropionyl derivative of formula (VI):

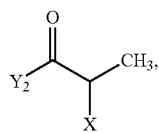
(VI)

at temperatures between −80° C. and +50° C., to form the heterocyclic compound of formula (I), wherein:

Y is selected from the group consisting of oxygen, sulphur and $NR_5$;

$R_1$, $R_2$, $R_3$ and $R_4$ are independently selected from the group consisting of hydrogen, methyl, ethyl, ($C_3$-$C_9$) aliphatic alkyl, ($C_3$-$C_9$)alicyclic alkyl, heteroaryl, heteroaryl($C_{1-3}$)alkyl, aryl, and aryl($C_1$-$C_3$)alkyl, optionally mutually combined to form an o-phenylene structure with the 1,3 imidazolidine ring, such as a benzo[d]-2,3-dihydro-1H-imidazole structure, and, such that when $R_1$ is coupled to $R_2$ and $R_3$ is coupled to $R_4$, they mutually combine to form an alkylene group or a cyclic spiro structure, such as ligands of heterocyclo 1,3-imidazolidine;

E is selected from the group consisting of oxygen and sulphur;

R is selected from the group consisting of hydrogen, methyl, ethyl, propyl, isopropyl, ($C_4$-$C_9$)aliphatic alkyl, ($C_3$-$C_9$)alicyclic alkyl, and 1-haloethyl(—CHX—$CH_3$) only when E is oxygen, aryl, heteroaryl, aryl($C_1$-$C_3$) alkyl, heteroaryl($C_1$-$C_3$)alkyl, ($C_1$-$C_9$)aliphatic alkyloxy, ($C_3$-$C_9$)alicyclic alkyloxy, aryloxy, heteroaryloxy, aryl($C_1$-$C_3$)alkyloxy, heteroaryl($C_1$-$C_3$)alkyloxy, ($C_1$-$C_9$)aliphatic alkylthio, ($C_3$-$C_9$)alicyclic alkylthio, arylthio, heteroarylthio, aryl($C_1$-$C_3$)alkylthio, and heteroaryl($C_1$-$C_3$)alkylthio;

$Y_1$ is a nucleofugal group;

the first and second base are independently selected from the group consisting of an alkali metal hydride, a ($C_1$-$C_4$)alkyllithium derivative, an aryllithium derivative, a heteroaryllithium derivative and an alkali metal;

X is a halogen selected from the group consisting of chlorine, bromine and iodine; and $Y_2$ is a nucleofugal group.

11. The process of claim 10, wherein:

the activated derivative of formula (V) is the 2-halopropionyl derivative of formula (VI); and the process forms at least one heterocyclic compound selected from the group consisting of for preparing the compounds (Ic), (Id), (Ie), and (If):

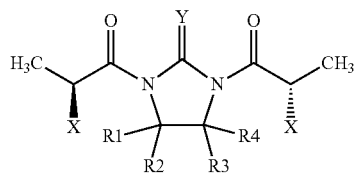
(Ic)

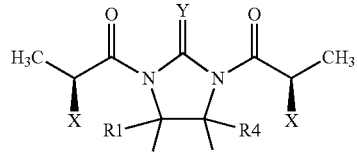
(Id)

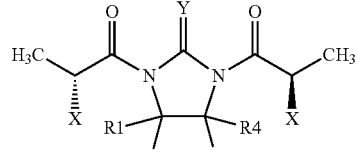
(Ie)

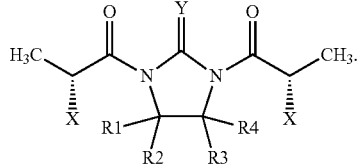
(If)

12. The process of claim 11, wherein:

the activated derivative of formula (V) and the 2-halopropionyl derivative of formula (VI) are both racemic or optically pure but mutual enantiomers; and the process further comprises separating product stereoisomers by chromatography to obtain the heterocyclic compound as a racemate or a pure stereoisomer.

13. A process for inverting the configuration of the stereocentres binding the substituent X in the compounds (Ic), (Id), (Ie) and (If) of claim 4, the process comprising catalyzed acid rebalancing followed by chromatographic separation to isolate resulting diastereoisomeric products.

14. The process of claim 13 wherein:

$R_1$, $R_2$, $R_3$ and $R_4$ of the compounds (Ic), (Id), (Ie) and (If) represent identical substituents; and the mesoforms (Id) and (If) are transformed into a corresponding racemate (Ic)+(Ie).

15. A process for preparing the compound of claim 5, the process comprising reacting a compound of formula (I):

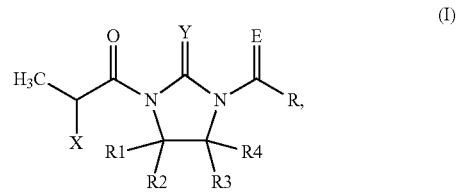
(I)

under Reformatsky conditions, in the presence of a reducing agent, with a compound of formula (III):

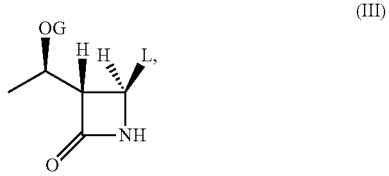
(III)

at temperatures between −50° C. and +150° C., to form the compound of formula (IIIb),
wherein:
X is a halogen selected from the group consisting of chlorine, bromine and iodine;
Y is selected from the group consisting of oxygen, sulphur and $NR_5$;
$R_5$ is ($C_1$-$C_9$)aliphatic, ($C_3$-$C_9$)alicyclic, ($C_3$-$C_9$)heterocyclic, phenyl, aryl, or heteroaryl carrying up to three substituents selected from the group consisting of halogen, nitro group, and ($C_1$-$C_3$)alkoxy;
E is selected from the group consisting of oxygen and sulphur;
R is selected from the group consisting of hydrogen, methyl, ethyl, propyl, isopropyl, ($C_4$-$C_9$)aliphatic alkyl, ($C_3$-$C_9$)alicyclic alkyl, and 1-haloethyl(—CHX—$CH_3$) only when E is oxygen, aryl, heteroaryl, aryl($C_1$-$C_3$) alkyl, heteroaryl($C_1$-$C_3$)alkyl, ($C_1$-$C_9$)aliphatic alkyloxy, ($C_3$-$C_9$)alicyclic alkyloxy, aryloxy, heteroaryloxy, aryl($C_1$-$C_3$)alkyloxy, heteroaryl($C_1$-$C_3$)alkyloxy, ($C_1$-$C_9$)aliphatic alkylthio, ($C_3$-$C_9$)alicyclic, alkylthio, arylthio, heteroarylthio, aryl($C_1$-$C_3$)alkylthio, and heteroaryl($C_1$-$C_3$)alkylthio;
$R_1$, $R_2$, $R_3$ and $R_4$ are independently selected from the group consisting of hydrogen, methyl, ethyl, ($C_3$-$C_9$) aliphatic alkyl, ($C_3$-$C_9$)alicyclic alkyl, heteroaryl, heteroaryl($C_1$-$C_3$)alkyl, aryl, and aryl($C_1$-$C_3$)alkyl, optionally mutually combined to form an o-phenylene structure with the 1,3 imidazolidine ring, such as a benzo [d]-2,3-dihydro-1H-imidazole structure, and, such that when $R_1$ is coupled to $R_2$ and $R_3$ is coupled to $R_4$, they mutually combine to form an alkylene group or a cyclic spiro structure, such as ligands of heterocyclo 1,3-imidazolidine;
G is selected from the group consisting of hydrogen, ($C_1$-$C_4$)alkyl, methoxymethyl, methylthiomethyl, allyl, propargyl, methoxyethoxymethyl, ($C_1$-$C_9$)dialkylboryl, 9-borabicyclonon-9-yl, 2,2,2-trichloroethoxymethyl, tetrahydropyranyl, a substituted ethyl group selected from the group consisting of 1-ethoxyethyl, 1-methyl-1-methoxyethyl, and trichloroethyl, an aryl-substituted methyl group selected from the group consisting of phenylmethyl, diphenylmethyl, triphenylmethyl, p-methoxyphenylmethyl, o-nitrophenylmethyl, p-nitrophenylmethyl, and p-chlorophenylmethyl, a substituted silyl group selected from the group consisting of trimethylsilyl, triethylsilyl, t-butyldimethylsilyl, and t-butyldiphenylsilyl group, formyl, ($C_1$-$C_5$)alkanoyl, halogenated ($C_1$-$C_3$)alkanoyl, an aryloyl selected from the group consisting of benzoyl, p-methylbenzoyl, and naphthoyl, ($C_1$-$C_4$)alkoxycarbonyl, halogenated ethoxycarbonyl, ($C_3$-$C_5$)alkenylcarbonyl and arylmethoxycarbonyl; and
L is a nucleofugal ligand selected from the group consisting of halogen, formyloyloxy, acetoxy, ($C_2$-$C_5$)alkylcarbonyloxy, ($C_3$-$C_9$)cycloalkylcarbonyloxy, a ($C_1$-$C_5$) acyloxy that is unsaturated or halogenated at a position vicinal to the carbonyl, arylcarbonyloxy, ($C_1$-$C_7$)alkylsulphonyloxy, arylsulphonyloxy, ($C_1$-$C_7$)alkylsulphonyl, arylsulphonyl, ($C_1$-$C_7$)alkylsulphinyl, and arylsulphinyl, $C_7$)alkylsulphenyl and arylsulphenyl,
with the provisos that:
1 to 5 molar equivalents of powdered zinc is present with respect to the compound of formula (III); and
0.5 to 3 molar equivalents of the compound of formula (I) is present with respect to the compound of formula (III).

16. A process for preparing an intermediate of formula (IIIe):

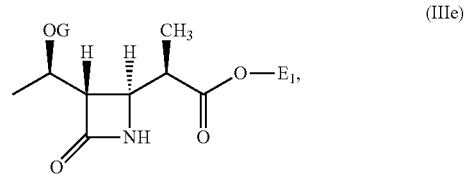

the process comprising reacting the compound of claim 5 with an alcoholate for about 1 hour at a temperature between −20° C. and +50° C. to form the intermediate of formula (Me),
wherein:
G is selected from the group consisting of hydrogen, ($C_1$-$C_4$)alkyl, methoxymethyl, methylthiomethyl, allyl, propargyl, methoxyethoxymethyl, ($C_1$-$C_9$)dialkylboryl, 9-borabicyclonon-9-yl, 2,2,2-trichloroethoxymethyl, tetrahydropyranyl, a substituted ethyl group selected from the group consisting of 1-ethoxyethyl, 1-methyl-1-methoxyethyl, and trichloroethyl, an aryl-substituted methyl group selected from the group consisting of phenylmethyl, diphenylmethyl, triphenylmethyl, p-methoxyphenylmethyl, o-nitrophenylmethyl, p-nitrophenylmethyl, and p-chlorophenylmethyl, a substituted silyl group selected from the group consisting of trimethylsilyl, triethylsilyl, t-butyldimethylsilyl, and t-butyldiphenylsilyl group, formyl, ($C_1$-$C_5$)alkanoyl, halogenated ($C_1$-$C_3$)alkanoyl, an aryloyl selected from the group consisting of benzoyl, p-methylbenzoyl, and naphthoyl, ($C_1$-$C_4$)alkoxycarbonyl, halogenated ethoxycarbonyl, ($C_3$-$C_5$)alkenylcarbonyl and arylmethoxycarbonyl; and
$E_1$ is selected from the group consisting of ($C_1$-$C_4$)alkyl, allyl, arylmethyl, diarylmethyl, and triarylmethyl; and
the alcoholate is selected from the group consisting of ($C_1$-$C_4$)aliphatic alcoholate, arylmethoxylate, diarylmethoxylate, and triarylmethoxylate of an alkali metal.

17. A process for preparing a compounds of formula (II);

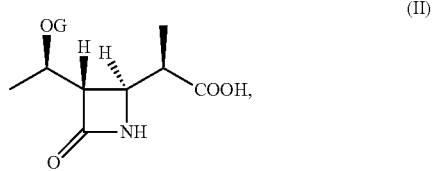

the process comprising reacting the compound of claim 5 with 1 to 20 molar equivalents of hydrogen peroxide in the presence of from 1 to 10 molar equivalents of an alkali metal hydroxide, with respect an amount of the compound of claim 5, in an aqueous organic solvent, at a temperature between −10° C. and +30° C. and, after the reacting, adding a reducing agent, to form the compound of formula (II),
wherein:
G is selected from the group consisting of hydrogen, ($C_1$-$C_4$)alkyl, methoxymethyl, methylthiomethyl, allyl, propargyl, methoxyethoxymethyl, ($C_1$-$C_9$)dialkylboryl, 9-borabicyclonon-9-yl, 2,2,2-trichloroethoxymethyl, tetrahydropyranyl, a substituted ethyl group selected from the group consisting of 1-ethoxyethyl, 1-methyl- 1-methoxyethyl, and trichloroethyl, an aryl-substituted methyl group selected from the group consisting of phenylmethyl, diphenylmethyl, triphenylmethyl, p-methoxyphenylmethyl, o-nitrophenylmethyl, p-nitrophenylmethyl, and p-chlorophenylmethyl, a substituted silyl group selected from the group consisting of trimethylsilyl, triethylsilyl, t-butyldimethylsilyl, and t-butyldiphenylsilyl group, formyl, $(C_1$-$C_5)$alkanoyl, halogenated $(C_1$-$C_3)$alkanoyl, an aryloyl selected from the group consisting of benzoyl, p-methylbenzoyl, and naphthoyl, $(C_1$-$C_4)$alkoxycarbonyl, halogenated ethoxycarbonyl, $(C_3$-$C_5)$alkenylcarbonyl and arylmethoxycarbonyl; and the aqueous organic solvent is selected from the group consisting of dioxane, tetrahydrofuran, N,N-dimethylformamide, $(C_1$-$C_4)$aliphatic alcohol, N,N-dimethylacetamide and N-methylpyrrolidone.

18. The process of claim 10, wherein the first and second aprotic inert solvent are independently selected from the group consisting of tetrahydrofuran, dioxane, 1,2-dimethoxyethane, a $C_6$ alicyclic hydrocarbon, a $(C_6$-$C_{10})$aliphatic hydrocarbon, a benzene, an $(C_1$-$C_3)$alkylsubstituted benzene, a $(C_1$-$C_3)$dialkylsubstituted benzene, a $(C_1$-$C_3)$ trialkylsubstituted benzene, a halogenated $(C_1$-$C_3)$aliphatic hydrocarbon, glyme, diglyme, a di$(C_1$-$C_4)$alkylether, N,N-dimethylacetamide, N,N-dimethylformamide, N-methylpyrrolidone and hexamethylphosphoramide.

* * * * *